(12) United States Patent
Mallo et al.

(10) Patent No.: US 11,439,599 B2
(45) Date of Patent: Sep. 13, 2022

(54) SCORED TABLET

(71) Applicant: CEVA SANTE ANIMALE, Libourne (FR)

(72) Inventors: Nadège Mallo, Laval (FR); Philippe Jolivet, Laval (FR); Mickael Venel, Laval (FR); Rosita Garcia, Laval (FR)

(73) Assignee: CEVA SANTE ANIMALE, Libourne (FR)

( * ) Notice: Subject to any disclaimer, the term of this patent is extended or adjusted under 35 U.S.C. 154(b) by 0 days.

(21) Appl. No.: 16/615,833

(22) PCT Filed: May 22, 2018

(86) PCT No.: PCT/FR2018/051223
§ 371 (c)(1),
(2) Date: Nov. 22, 2019

(87) PCT Pub. No.: WO2018/215723
PCT Pub. Date: Nov. 29, 2018

(65) Prior Publication Data
US 2020/0206140 A1 Jul. 2, 2020

(30) Foreign Application Priority Data
May 23, 2017 (FR) ........................................ 1754581

(51) Int. Cl.
*A61K 9/20* (2006.01)
(52) U.S. Cl.
CPC .................... *A61K 9/2072* (2013.01)

(58) Field of Classification Search
CPC .................................................. A61K 9/2072
See application file for complete search history.

(56) References Cited

U.S. PATENT DOCUMENTS

| 7,985,419 | B1* | 7/2011 | Parikh | A61K 9/2072 |
|---|---|---|---|---|
| | | | | 424/464 |
| 2006/0228409 | A1* | 10/2006 | Miyabe | A61K 9/2072 |
| | | | | 424/464 |

FOREIGN PATENT DOCUMENTS

| EP | 1 568 362 | 8/2005 | | |
|---|---|---|---|---|
| EP | 1568362 A1 * | 8/2005 | ........... | A61K 9/2072 |

OTHER PUBLICATIONS

EP-1568362-A1 (Espacenet English translation, downloaded Aug. 2021) (Year: 2021).*
Written Opinion in International Application No. PCT/FR2018/051223, Sep. 5, 2018, pp. 1-5.

* cited by examiner

*Primary Examiner* — Mark V Stevens
(74) *Attorney, Agent, or Firm* — Saliwanchik, Lloyd & Eisenschenk

(57) ABSTRACT

The invention relates to a scored tablet (1) comprising a convex upper face (2), an at least partially concave lower face (3) and a side wall (4) extending between the upper and lower faces; two score grooves (5, 6) are formed in the concave lower face, said grooves being perpendicular to one another and continuous with score slits (8, 9, 10, 11) located in the side wall.

14 Claims, 2 Drawing Sheets

SCORED TABLET

CROSS-REFERENCE TO RELATED APPLICATION

Figure 1A:
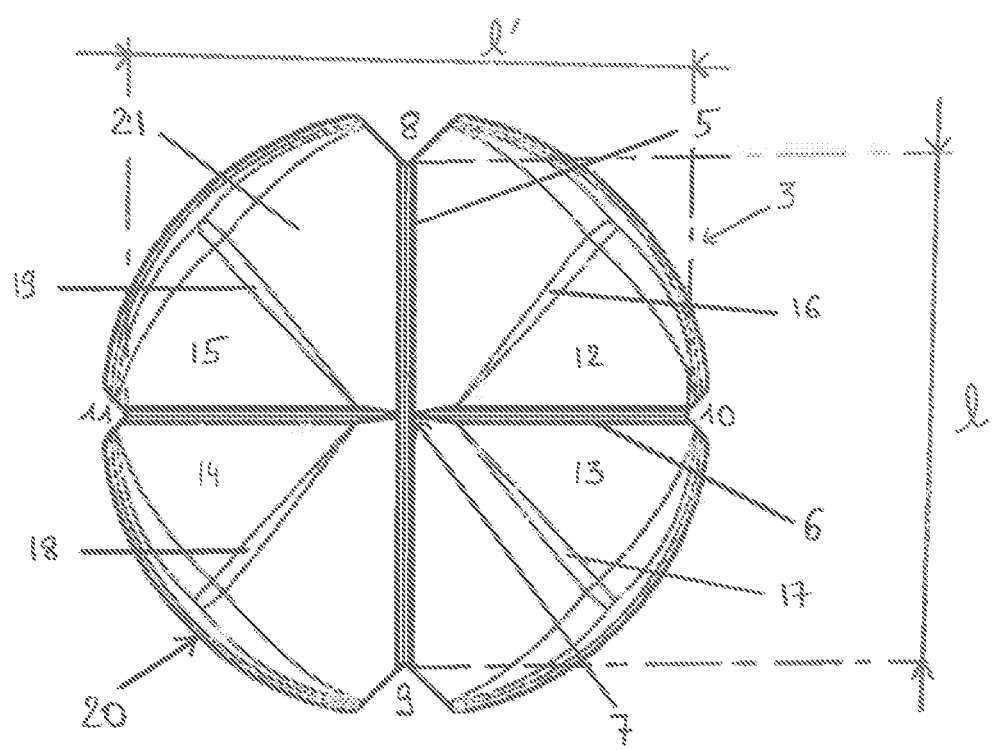

This application is the U.S. national stage application of International Patent Application No. PCT/FR2018/051223, filed May 22, 2018.

The invention relates to a scored tablet which can be easily cleaved, into two or four parts, by simple pressure exerted on said tablet. A subject of the invention is more particularly such a scored tablet for veterinary use, in particular for dogs and cats.

Tablets have been used for a long time to orally administer a solid pharmaceutical composition to a subject. Tablets are generally swallowed or chewed, in order to release the active substance(s) that they contain in the organism. Usually, tablets are obtained by agglomerating, by compression, a volume of particles containing the active substance(s). Thus, a given type of tablet, of defined shape and weight, systematically comprises the same amount of active substances.

Insofar as the amount of active substances to be administered can vary from one subject to another, in particular according to the weight of the subject, laboratories have developed scored tablets, which make it possible to divide in half or in quarters said tablet and thereby the amount of active substances.

In the veterinary field, because of the diversity of animals in terms of weights, the scoring of tablets is of particular importance. Indeed, one and the same tablet may be, for example, intended for dogs and cats, which have very variable builds. It is thus necessary to be able to adjust the dose of active substances to be administered.

Scored tablets usually have one or two lines debossed in the thickness of said tablets in order to facilitate cleavage along said lines. However, the cleavage step is often awkward. The pressure to be exerted is all the more difficult to apply since the tablet is small and it is not easy to hold it between the fingers. This results in inaccurate and uneven cleavage, consequently leading to inaccuracies in the amounts of active substances contained in the tablet portions.

An objective of the invention is to at least partially solve the problems associated with the scoring of tablets, by providing a tablet capable of being divided into two or into four identical parts by exerting one or two pressures on said tablet. For this, the tablet according to the invention has a face that overall is concave, intended to be applied against a planar surface, and a convex face on which the pressure must be exerted. Two cleavage lines perpendicular to one another are debossed in the concave face and extend as far as into the exterior outline of the tablet, thus delimiting the tablet halves and quarters. The shape of the tablet associated with the cleavage lines which extend on either side of the tablet contributes to ensuring accurate and easy cleavage. The tablet according to the invention makes it possible to obtain tablet halves or quarters with little or no weight dispersion. Advantageously, the tablet according to the invention also has a round, or cylindrical circular, shape making industrial-scale production easier. The manufacture of such round-shaped tablets by compression enables a gain in terms of productivity of 30 to 50% compared with other, more complex, tablet shapes, such as the cloverleaf shape.

A subject of the invention is thus a scored tablet comprising a convex upper face, an at least partially concave lower face and a side wall extending between the upper and lower faces; two score grooves are formed in the concave lower face, said grooves being perpendicular to one another and continuous with score slits located in the side wall.

According to the invention, the term "lower face" denotes the face intended to be applied against a surface during the tablet cleavage step, as opposed to the "upper face".

In one particular embodiment, the angle of curvature of the concave portion of the lower face is between 150° and 170°, preferentially equal to 165°, +/−5°.

The score grooves and score slits are debossed in the thickness of the tablet, so as to delimit four triangles of identical or substantially identical shape and size. The "thickness" of the tablet is intended to mean the dimension extending perpendicularly to the plane of the lower or upper face of the tablet.

According to the invention, the tablet can be divided into two half-tablets by exerting a first pressure on the convex face. The tablet is broken in two along a first score groove. If necessary, each half-tablet can again be broken in two, along the second score groove, by exerting a pressure on the convex face of said half-tablet. Four perfectly identical tablet portions of substantially triangular shape are thus obtained.

Advantageously, the tablet according to the invention has a cylindrical circular shape. Such a conformation facilitates in particular the industrial packaging of the tablets in blister packs. In another embodiment, the tablet can have an oval, square, rectangular etc., shape.

In one particular embodiment, the score grooves of the lower face have a V-shaped cross section. Advantageously, the V-shaped cross section has an angle of opening of between 40° and 100°, preferentially equal to 80°+/−5°. The V-shaped cross section extends in a plane of cleavage perpendicular to the plane of the lower face of the tablet.

Advantageously, the score grooves of the lower face have a depth of between $1/5$ and $3/10$ of the thickness of the tablet. The term "depth" is intended to mean the dimension extending in a plane perpendicular to the plane of the lower face.

In one particular embodiment, one of the score grooves is continuous and the other score groove is discontinuous. Such a discontinuity promotes the first breaking of the tablet along the continuous score groove. Preferentially, the discontinuous score groove stops upstream of the intersection of the score grooves. The discontinuous score groove can otherwise have one or more successive interruptions, until it forms for example a dashed line.

In one particular embodiment, the two score grooves of the lower face have different lengths. The term "length" is intended to mean the dimension extending along the largest dimension of the tablet. This conformation promotes the first breaking of the tablet along the shortest score groove. For example, two of the score slits extending into the extension of one of the score grooves are embossed more deeply in the diameter of the tablet than the other two score slits, so as to reduce as much the length of the associated score groove.

According to the invention, the score grooves divide the tablet into four substantially identical triangles. In one particular embodiment, the lower face of each of the triangles has an edge extending from the outer rim of the tablet, to a score groove, at the intersection or upstream of the intersection of said score grooves. The term "edge" is intended to mean the protruding angle formed by the meeting of the two surfaces bordering said angle. Alternatively, the lower face of each of the triangles is bowed. Thus, the lower face of the tablet has discontinuous bearing surfaces when it is in contact with a planar surface. The lower face then has a partial concavity, extending mainly along one of the score grooves. Alternatively, the lower face has a uniform concave surface.

In one particular embodiment, an outer rim of the lower face is beveled, along the side wall.

In one particular embodiment, the score slits of the side wall have a V-shaped cross section. Advantageously, the V-shaped cross section has an opening angle of between 70° and 120°, preferentially equal to 90°+/−5°. The V-shaped cross section extends in a cleavage plane parallel to the plane of the lower face of the tablet. In one implementation example, the score slit opening angles are all equal. In another implementation example, the score slit opening angles are equal in pairs. More specifically, the opening angles of the score slits extending into the extension of one same score groove are equal, but different than the opening angles of the score slits extending into the extension of the other same score groove.

The scored tablet according to the invention advantageously has a largest dimension between 10 and 22 mm, preferentially between 16 and 20 mm, more preferentially of 18 mm. In one particular embodiment, the tablet according to the invention has a largest dimension of 10 mm, 12 mm, 14 mm, 16 mm, 18 mm, 20 mm, or 22 mm, +/−0.5 mm. In the case where the tablet has a general cylindrical circular shape, the largest dimension extends from the largest diameter of said tablet. The thickness of such a tablet is between 0.4 and 1 mm, preferentially 0.45 and 0.85 mm, and the depth of the score grooves is between 0.1 and 0.3 mm.

The invention will be understood more clearly on reading the description which follows and on examining the figures which accompany it. They are presented by way of information and are in no way limiting with regard to the invention. The figures represent:

FIG. 1: a schematic representation view from above (A) and from below (B) of a scored tablet according to one implementation example of the invention;

FIG. 2: two schematic side-view representations (A and B) of a scored tablet according to one implementation example of the invention.

An objective of the invention is to provide a scored tablet that can be cleaved, if required, into two or four equal parts, in order to be able to easily adjust the amount of active substance to be administered as a function of the dosage regime. One and the same type of tablet can thus be administered to various users, and more particularly various animals, having in particular a broad weight range, since it is possible to administer all, half or a quarter of the dose of active substances that is initially contained in the tablet. The scored tablet according to the invention has score grooves and slits making it possible to guarantee a homogeneous cleavage, by simple pressure, in order to obtain tablet halves or quarters comprising a controlled amount of active substance.

In the example represented in FIGS. 1 and 2, the tablet has an overall circular shape. Of course, other shapes can be envisioned, and in particular an oval, rectangular or square shape.

The tablet 1 comprises an upper face 2, a lower face 3 and a side face 4 extending perpendicularly between the two upper 2 and lower 3 faces, that are substantially circular. The upper face 2 is convex, as can in particular be seen in FIGS. 2A and 2B, while the lower face 3 is concave overall.

As can be seen in FIG. 1A, the tablet 1 according to the invention has, on its lower face 3, two score grooves 5, 6, debossed in the thickness of said lower face 3. The term "thickness" is intended to mean the dimension extending perpendicularly to the plane of observation of the lower face 3. The score grooves 5, 6 are perpendicular to one another. A first score groove 5 extends continuously in a diameter of the lower face 3. The second score groove 6 is, for its part, discontinuous. More specifically, the second score groove 6 stops at the intersection 7 between the two score grooves, located at the center of the lower face 3 of the tablet 1.

Figure 2A:
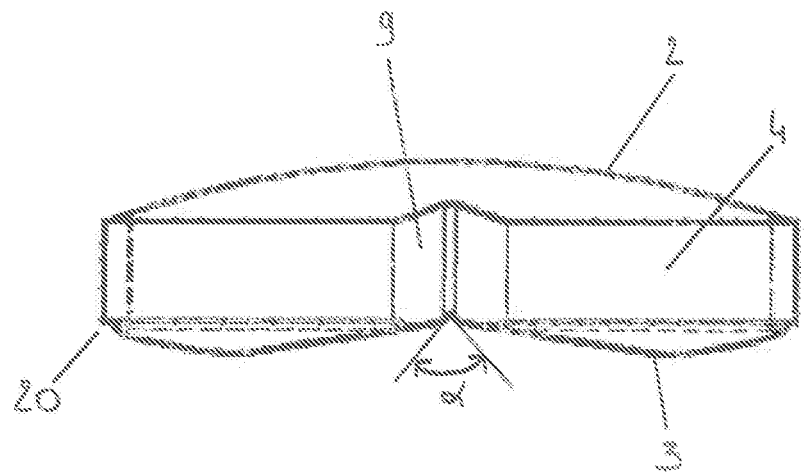
Figure 2B:
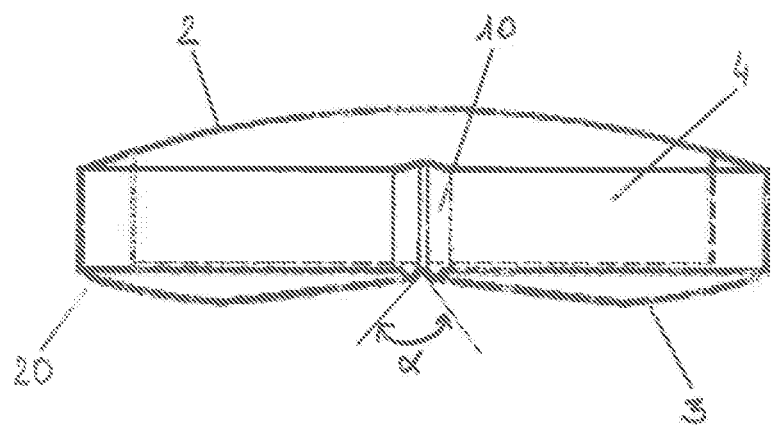

The score grooves 5, 6 have a V-shaped cross section, in such a way that the width of said score grooves decreases from the external surface of the lower face 3 to the interior of the tablet 1. The term "width" is intended to mean the dimension of the grooves extending perpendicularly to the largest dimension and in the same plane. Of course, it is possible to make score grooves which have a square or rectangular cross section, for example, in such a way that the width of said grooves is constant. The opening angle α of the score grooves 5, 6 is 80°, +/−5° (FIGS. 2A and 2B).

In the example represented in FIGS. 1 and 2, the score grooves 5, 6 have identical depths, but it is possible to envision different depths between the two grooves. In this case, the continuous score groove advantageously has the greatest depth. It is also possible to envision a variable depth along a score groove, in such a way for example as to make a greater groove depth at the center of the tablet.

Figure 1B:
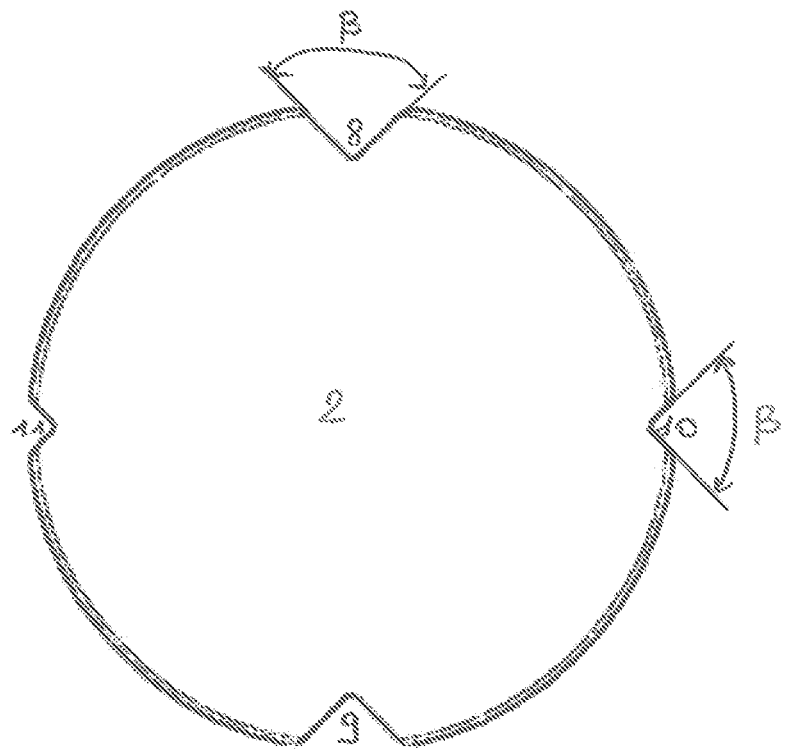

The score grooves 5, 6 made on the lower face 3 of the tablet 1 extend on the side face 4, in such a way as to form thereon score slits 8, 9, 10, 11. The score slits 8, 9, 10, 11 have a V-shaped cross section, an opening angle β of which is approximately 90°, +/−5° (FIG. 1B).

The two score grooves 5, 6 have different lengths 1 and 1'. More specifically, the continuous score groove 5 has a length 1 smaller than the length 1' of the discontinuous score groove 6. In order to obtain a such a difference in length, although the tablet has a circular general shape, the score slits 8, 9 extending on the side face 4 of the tablet 1 and in the extension of one of the score grooves 5 are deeper than the score slits 10, 11 extending into the extension of the other score groove 6.

As can be seen in FIG. 1A, the score grooves 5, 6 and the score slits 8, 9, 10, 11 make it possible to divide the tablet 1 into four triangles 12, 13, 14, 15 that are identical in terms of dimensions.

In the implementation example described here, the lower face 3 has various slopes. More specifically, each triangle 12, 13, 14, 15 comprises an edge 16, 17, 18, 19 extending from the external edge 20 of the lower face 3 to the discontinuous score groove 6. Each triangle 12, 13, 14, 15 thus has descending slopes from the corresponding edge 16, 17, 18, 19 to the score grooves. Advantageously, the edges 16, 17, 18, 19 cleave the discontinuous score groove 6 upstream of the intersection 7 with the continuous score groove 5. The lower face 3 is thus partially concave. More specifically, the lower face 3 has a concavity zone 21 extending substantially along the continuous score groove 5, such that the thickness of the tablet 1 is smallest at the intersection 7 between the score grooves 5, 6. The concavity zone 21 is more specifically delimited by the edges 16, 17, 18, 19, from said edges up to the center of the tablet 1.

The angle of curvature a of the concavity zone is 165°, +/−5° (FIG. 2B).

Moreover, the outer rim 20 of the lower face 3 of the tablet 1 is beveled.

All of the arrangements presented above promote the cleavage of the tablet 1, successively, into tablet halves then quarters. For this, it is sufficient to have the tablet 1 on a preferentially planar surface, convex upper face 2 facing upward. A pressure exerted by a finger on the convex upper face 2 of the tablet 1 makes it possible to divide the tablet into two identical parts, the cleavage taking place along the continuous score groove 5. If it proves to be necessary, it is then possible to exert a pressure with the finger on the upper face of a half-tablet, in order to cleave said half-tablet in two, along the discontinuous score groove 6. Two identical tablet quarters are thus obtained.

The invention claimed is:

1. A scored tablet comprising a convex upper face, an at least partially concave lower face and a side wall extending between the upper and lower faces and score grooves formed in the concave lower face,
  wherein said score grooves are perpendicular to one another and continuous with score slits located in the side wall,
  wherein one of the score grooves is continuous, thus extending as a single cut between two score slits of the continuous score groove, and the other score grooves are discontinuous and terminate at said continuous groove, and
  wherein each score slit has a V-shaped cross section, each score slit of the continuous score groove having a deeper extension within the scored tablet than the extension of the score slit of the discontinuous score groove so that the length of the continuous score groove is smaller than the length of the discontinuous score grooves to promote the first breaking of the tablet along the continuous score groove.

2. The scored tablet as claimed in claim 1, said tablet having a cylindrical circular shape.

3. The scored tablet as claimed in claim 1, wherein the score grooves of the lower face have a V-shaped cross section.

4. The scored tablet as claimed in claim 3, wherein the V-shaped cross section has an opening angle α of between 40° and 100°.

5. The scored tablet as claimed in claim 3, wherein the V-shaped cross section has an opening angle α equal to 80°+/−5°.

6. The scored tablet as claimed in claim 1, wherein the score grooves of the lower face have a depth of between 1/5 and 3/10 of the thickness of the tablet.

7. The scored tablet as claimed in claim 6, wherein the score grooves divide the tablet into four substantially identical triangles, the lower face of each of the triangles having an edge extending from the outer rim to a score groove, upstream of the intersection of said score grooves.

8. The scored tablet as claimed in claim 6, wherein an outer rim of the lower face is beveled.

9. The scored tablet as claimed in claim 6, wherein the score slits of the side wall have a V-shaped cross section.

10. The scored tablet as claimed in claim 9, wherein the V-shaped cross section of the score slits of the side wall has an opening angle β of between 70° and 120°.

11. The scored tablet as claimed in claim 9, wherein the V-shaped cross section of the score slits of the side wall has an opening angle β equal to 90°+/−5°.

12. The scored tablet as claimed in claim 6, wherein said tablet has a largest diameter of between 10 and 22 mm.

13. The scored tablet as claimed in claim 6, said tablet having a cylindrical circular shape, wherein the score grooves divide the tablet into four substantially identical triangles, the lower face of each of the triangles having an edge extending from the outer rim to a score groove, upstream of the intersection of said score grooves.

14. The scored tablet as claimed in claim 7, wherein each edge extends as far as the discontinuous score groove, upstream of the intersection of said score grooves.

* * * * *